(12) United States Patent
Maritan et al.

(10) Patent No.: US 10,159,826 B2
(45) Date of Patent: Dec. 25, 2018

(54) ADAPTOR FOR A DRUG DELIVERY DEVICE AND METHOD FOR MOUNTING SAID ADAPTOR THEREON

(71) Applicant: Becton Dickinson France, Le Pont de Claix (FR)

(72) Inventors: Lionel Maritan, Pierre-Chatel (FR); Gilbert Poncon, Pommiers la Placette (FR); Guillaume Grunhut, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 278 days.

(21) Appl. No.: 14/435,035

(22) PCT Filed: Oct. 11, 2013

(86) PCT No.: PCT/EP2013/071231
§ 371 (c)(1),
(2) Date: Apr. 10, 2015

(87) PCT Pub. No.: WO2014/057071
PCT Pub. Date: Apr. 17, 2014

(65) Prior Publication Data
US 2015/0283372 A1 Oct. 8, 2015

(30) Foreign Application Priority Data
Oct. 12, 2012 (EP) .................... 12306260

(51) Int. Cl.
*A61M 39/10* (2006.01)
*A61J 1/20* (2006.01)
*A61M 5/31* (2006.01)

(52) U.S. Cl.
CPC ........ *A61M 39/1011* (2013.01); *A61J 1/2051* (2015.05); *A61J 1/2065* (2015.05);
(Continued)

(58) Field of Classification Search
CPC .............. A61M 39/10; A61M 39/1011; A61M 2005/3104; A61M 2039/1077;
(Continued)

(56) References Cited

U.S. PATENT DOCUMENTS 5,419,777 A 5/1995 Hofling
5,489,205 A 2/1996 Davis et al.
(Continued)

FOREIGN PATENT DOCUMENTS

EP 2182265 A1 5/2010
JP 08-506978 A 7/1996
(Continued)

*Primary Examiner* — Nathan R Price
*Assistant Examiner* — Anh Bui
(74) *Attorney, Agent, or Firm* — The Webb Law Firm

(57) ABSTRACT

The invention relates to an adaptor for a distal tip of a drug delivery device. The adaptor includes an inner ring having retaining means capable of exerting a radial inward force on said distal tip and of switching from a free configuration to a locked configuration, in which the radial inward force exerted on said conical distal tip limits the axial movement of the adaptor. The adaptor further includes compressing means movable axially with respect to said retaining means between a proximal position, in which said compressing means does not exert a centripetal pressure on said retaining means, and a distal position, in which centripetal pressure is exerted on said retaining means. The invention further relates to a drug delivery device comprising such an adaptor and to a method for mounting said adaptor on said drug delivery device.

13 Claims, 2 Drawing Sheets

(52) U.S. Cl.
CPC ............ *A61M 5/31* (2013.01); *A61M 5/3134* (2013.01); *A61M 39/10* (2013.01); *A61J 1/2048* (2015.05); *A61J 1/2096* (2013.01); A61M 2005/3103 (2013.01); A61M 2005/3104 (2013.01); *A61M 2039/1027* (2013.01); *A61M 2039/1033* (2013.01); *A61M 2039/1077* (2013.01); *A61M 2202/0007* (2013.01); *A61M 2205/02* (2013.01); *A61M 2207/00* (2013.01); Y10T 29/49863 (2015.01)

(58) Field of Classification Search
CPC .... A61M 2039/1027; A61M 2039/1033; A61J 1/2096; A61J 1/2048; A61J 1/2055; A61J 1/2065; A61J 1/2051
See application file for complete search history.

(56) References Cited

U.S. PATENT DOCUMENTS

| | | | |
|---|---|---|---|
| 5,509,911 A * | 4/1996 | Cottone, Sr. | A61M 39/1055 285/315 |
| 2002/0173748 A1 * | 11/2002 | McConnell | A61J 1/2096 604/167.02 |
| 2006/0033331 A1 | 2/2006 | Ziman | |
| 2009/0177182 A1 | 7/2009 | Hickingbotham et al. | |
| 2010/0176584 A1 | 7/2010 | Ito et al. | |
| 2010/0327010 A1 * | 12/2010 | Manera | B65D 47/2031 141/357 |
| 2012/0157928 A1 | 6/2012 | Mermet | |
| 2012/0289929 A1 | 11/2012 | Boyd et al. | |
| 2014/0012204 A1 | 1/2014 | Bosshardt et al. | |

FOREIGN PATENT DOCUMENTS

| | | |
|---|---|---|
| JP | 2010201177 A | 9/2010 |
| RU | 2139104 C1 | 10/1999 |
| RU | 2139105 C1 | 10/1999 |
| RU | 2460546 C2 | 9/2012 |
| WO | 2010140019 A1 | 12/2010 |
| WO | 2010150042 A1 | 12/2010 |
| WO | 2012049532 A1 | 4/2012 |

* cited by examiner

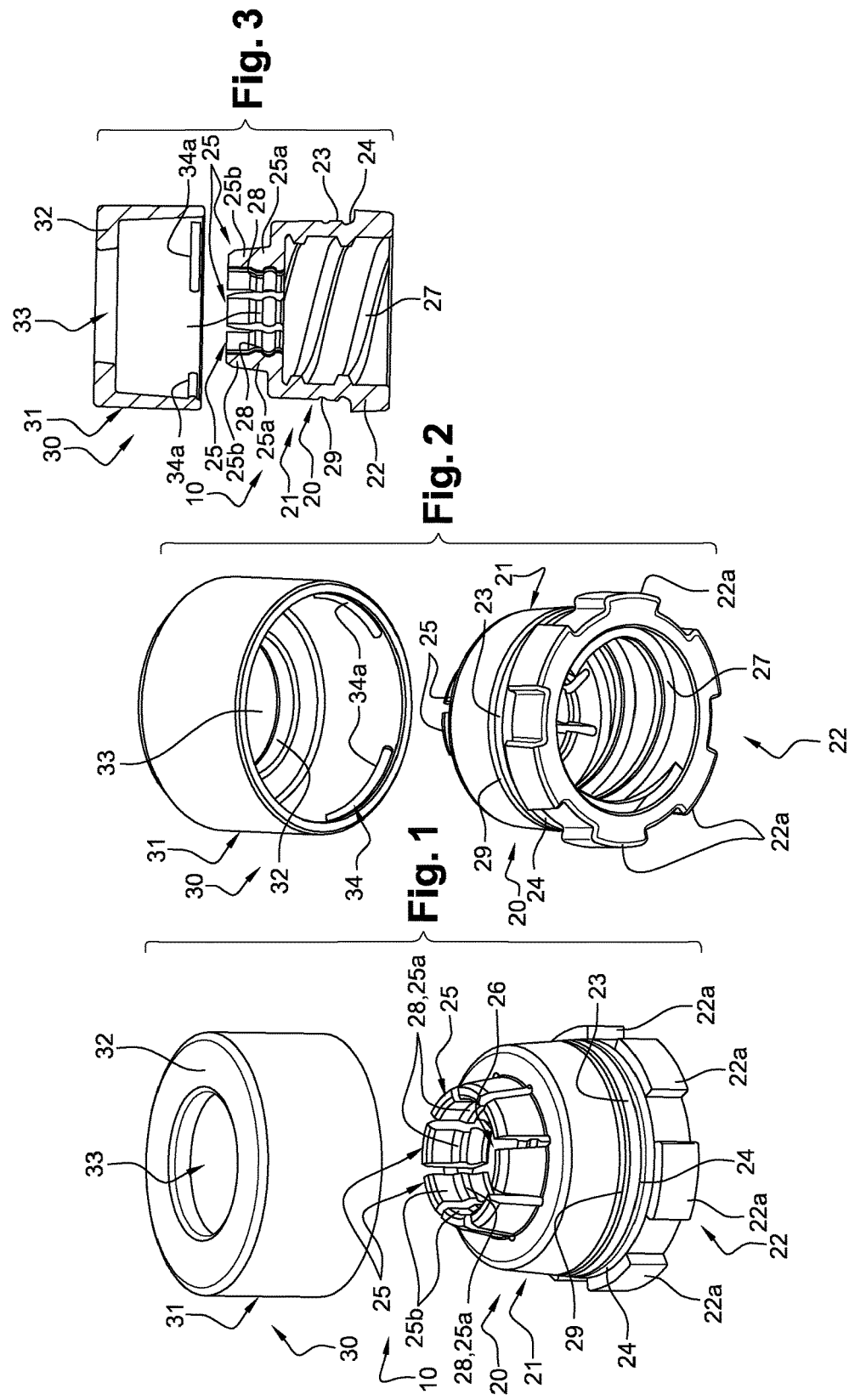

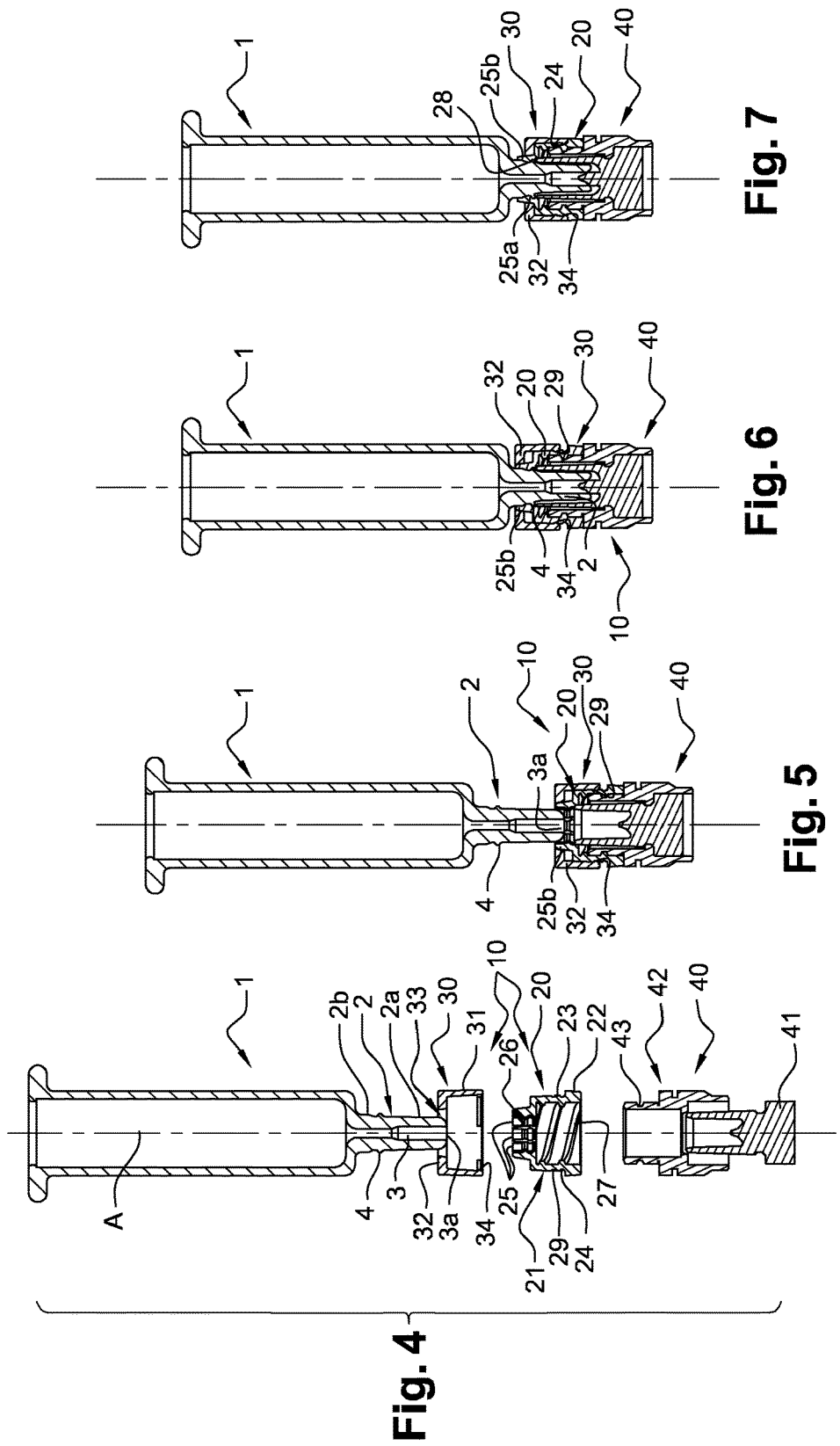

ADAPTOR FOR A DRUG DELIVERY DEVICE AND METHOD FOR MOUNTING SAID ADAPTOR THEREON

CROSS-REFERENCE TO RELATED APPLICATIONS

This application is the United States national phase of International Application No. PCT/EP2013/071231 filed Oct. 11, 2013, and claims priority to European Patent Application No. 12306260.6 filed Oct. 12, 2012, the disclosures of which are hereby incorporated in their entirety by reference.

BACKGROUND OF THE INVENTION

Field of the Invention

The present invention relates to an improved adaptor, for example a Luer lock adaptor, for use with a drug delivery device. The adaptor allows a safe connection between the drug delivery device and a connector to be coupled to the drug delivery device. The invention also relates to a drug delivery device provided with such an improved adaptor and to a method for mounting said adaptor on such a drug delivery device.

Description of Related Art

Various medical devices are known for transferring and/or storing medical fluids, such as syringes, needle assemblies, perfusion devices, transfusion devices and connectors such as for example IV (Intra Venous), IM (Intra Muscular), subcutaneous connectors. It is essential for safety reasons that these various medical devices can be assembled together correctly and securely. The use of specific adaptors between the various medical devices allows them to be assembled, ensuring a sealed connection and providing protection against the contamination of the medical liquid products they contain.

A conventional drug delivery device usually comprises a hollow body forming a container for a medical product: the distal end of the body forming the container usually comprises a tip in which an axial passageway is arranged and through which the said product is expelled from the container.

Conventional drug delivery devices typically are made of plastic or glass. Glass barrels are used for medications that are particularly susceptible to interact with ambient gases or with the container material(s). Glass barrels are also preferably used for medications that are pre-filled into the barrel and stored over a considerable period of time prior to use. When the drug delivery device and its distal tip are made of plastic material, the adaptor may be molded together with the distal tip, using the same material or one of a kind. Anyway, because of difficulty of manufacturing, glass barrels and glass distal tips in particular may require a separately formed adaptor to be mounted thereon. The adaptor should be securely mounted onto the distal tip of the drug delivery device to avoid its disconnection from the tip.

Usually, the adaptors are first mounted on the distal tip of the drug delivery device by friction force and the connector is then mounted on the free end of the adaptor, for example by screwing. In general, adaptors are provided with a radially expandable ring which is friction forced on the distal tip. The adaptor is then intended to remain immobile with respect to the distal tip by slip fit interengagement, by virtue of the friction force exerted by the ring on the distal tip.

The strength of the assembling of the adaptor on the distal tip depends firstly on the accuracy of the dimensions of the external surface of both the distal tip and the adaptor, secondly on the force used to engage the adaptor on the distal tip. Due to industrial tolerances, the assembling of the adaptor on the distal tip is therefore rather inaccurate and the strength of the assembling cannot be guaranteed. It may then occur that such interengagement is not secured enough.

SUMMARY OF THE INVENTION

In order to increase the reliability of such an assembly, it has been proposed to provide the distal tip with a groove the ring of the adaptor would get stuck in. Anyway, such solution is not desirable when the distal tip is made of glass material, because of glass forming difficulties, and also because it may increase the fragility of the distal tip.

Therefore, there is a need for an improved adaptor enabling to ensure a reliable assembling of the adaptor onto a drug delivery device. There is also a need of a drug delivery device provided with such adaptor.

Medical uses require specific assembling conditions to ensure that the drug delivery device is not contaminated. A suitable quality level is obtained by performing the assembling in clean rooms, under a specific grade, in which the drug delivery devices are washed, then siliconized to allow a better gliding of the stopper. However, the friction force connection of an adaptor onto the distal tip of a drug delivery device may be highly impacted by the presence of silicone that may inadvertently be applied on the outside surface of the distal tip.

There is therefore a need for an improved adaptor enabling a reliable assembling on the distal tip of a drug injection device. There is also a need of a drug delivery device provided with such adaptor.

Other problems have been reported concerning the use of adaptors with various drug delivery devices. Indeed, most of the adaptors that are available for use in the medical field for the purpose of connecting drug delivery devices with connectors are made of plastic material. The capability of deformation of such plastic material is influenced by aging and temperature conditions. In addition, plastic materials are sensitive to sterilization process.

First of all, the range of available plastic material usable in the medical field is limited in term of composition and color.

Secondly, it may happen that, for example after a certain time or after having been submitted to specific conditions like sterilization cycles and/or submission to different temperatures, elastic characteristics of the plastic material chosen are modified. As a consequence, the adaptor does not remain immobile with respect to the distal tip of the drug delivery device. Parts of the adaptor may be weakened by sterilization and may no longer ensure a sufficient tightening onto the distal tip, leading to an easy disconnection of the adaptor. Also, it may happen that the friction forces are not important enough to prevent the adaptor from rotating, particularly when the user tries to screw a connector on to the adaptor. It is therefore impossible for the user to determine whether the connector is well fitted in the adaptor or not and, as a consequence, whether the connector is well connected to the distal tip of the drug delivery device. An incorrect connection between the drug delivery device and the connector may cause the displacement of the adaptor and/or of the connector in regards to the drug delivery device, that could lead to product leakage and therefore incorrect doses administered to the patient as well as product waste. To overcome this problem and ensure right connection between the connector and the adaptor, when screwing the connector onto the adaptor, the user tends to hold the drug delivery device by the adaptor itself. The adaptor having a small size, it is difficult to handle it efficiently. During this operation, the user's fingers are close to the tip of the injection drug delivery device and to the axial passageway, increasing the risk of contamination of the medical liquid contained.

There is therefore a need for an improved adaptor enabling the use of a wider range of material while ensuring an efficient and reliable connection between the drug injection device and the connector. There is also a need of a drug delivery device provided with such adaptor.

In addition, there is a need for an adaptor that would be reliably secured on the distal tip of a drug delivery device, without having to modify the shape and/or the outer surface of said distal tip.

An aspect of the present invention is an adaptor intended to be mounted on the distal tip of a drug delivery device, allowing a safe connection between the drug delivery device and a connector intended to be connected onto the adaptor. In particular, the adaptor of the invention comprises securing means ensuring an optimal fixation of the adaptor onto the distal tip, so that said adaptor may not be disconnected from the distal tip in use.

A first aspect of the invention is an adaptor intended to be mounted on a distal tip of a drug delivery device, said distal tip defining an axial passage-way for the transfer of a product contained in said drug delivery device, said adaptor having a longitudinal axis A aligned on said axial passageway, the adaptor comprising connecting means for connecting said adaptor to a connector, said adaptor further comprising:

an inner ring capable of being engaged on said distal tip, said inner ring comprising retaining means capable of exerting a radial inward force on said distal tip once said adaptor is engaged on said distal tip,
wherein,
when said inner ring is engaged on said distal tip, said retaining means are capable of switching from a free configuration, in which the radial inward force they exert on said distal tip does not limit the axial movement of said adaptor with respect to said distal tip, to a locked configuration, in which the radial inward force they exert on said distal tip limits said axial movement,
the adaptor further comprising:
compressing means coupled to said inner ring, said compressing means being movable axially with respect to said retaining means between a proximal position, in which said compressing means do not exert a centripetal pressure on said retaining means and said retaining means are in their free configuration, and a distal position, in which said compressing means exert a centripetal pressure on said retaining means and said retaining means are in their locked configuration, and
releasable maintaining means for temporarily maintaining said compressing means in its proximal position with respect to said retaining means.

The adaptor of the invention may be used in particular for connecting a connector to a drug delivery device.

The risks of the adaptor of the invention being displaced and eventually misplaced on the distal tip of the drug delivery device it is intended to be mounted onto are therefore greatly limited. The adaptor of the invention therefore allows a reproducible connection of a connector and ensures that the connector is correctly positioned with respect to the drug delivery device.

Indeed, in the adaptor of the invention, the fastening of the adaptor onto the distal tip does not rely on the sole capability of the retaining means of the inner ring to exert a radial inward force on the distal tip. Indeed, an additional radial inward force, actually the centripetal pressure exerted by the compressing means, is added to the initial radial inward force generated by the retaining means. The global friction force exerted on the distal tip is therefore increased, and the adaptor is securely attached to the distal tip, with no danger that it detaches therefrom. In addition, because the global force exerted on the distal tip, when the retaining means are in their locked configuration, comes from two different sources, the retaining means on one hand, and the compressing means on the other hand, the force required by the user to position the adaptor may be applied in two steps. The right positioning of the adaptor is therefore facilitated and the risk to break the distal tip at the time the adaptor is mounted thereon is reduced.

In the present application, by "user" is meant a healthcare worker who may need to use the adaptor of the invention in order to connect thereon a connector such as an IV line, or alternatively it may be the drug delivery device manufacturer who will perform the mounting of the adaptor of the invention onto the distal tip of the drug delivery device, so as to provide the drug delivery device with the adaptor already mounted thereon. In such case, the mounting step further comprises the connection of a cap on the adaptor for ensuring safe closure of the drug delivery device in its storage position while there is no connector connected thereon. The mounting step at the manufacturer's premises may be completed automatically on assembly lines.

As a consequence, in the present application, "connector" means any device intended to be connected to the adaptor, either for allowing the transfer of a product from the drug delivery device to another medical device, such as a needle hub, a pocket drip, a vial, an IV (Intra Venous) line, an IM (Intra Muscular) line, or on the contrary for safely closing the filled drug delivery device before its use and for preventing any contamination, like for example a closure cap in the storage position of the drug delivery device.

Indeed, the adaptor of the invention is first engaged on the distal tip with the retaining means in their free configuration. Such a step does not require that a high force be produced by the user in order to place the adaptor onto the distal tip. Once the adaptor is positioned on the distal tip, with the retaining means in their free configuration, the user then moves the compressing means from their proximal position to their distal position. Here again, this step does not require that a high force be applied by the user. The integrity of the distal tip is therefore preserved. The adaptor of the invention therefore allows a safe connection of the adaptor to the distal tip, even if said distal tip is made of glass.

In addition, the fact that the compressing means of the adaptor of the invention are activated by a distal movement of these compressing means with respect to the retaining means ensures a safer fixing of the adaptor onto the distal tip and a better protection of the mounted assembly "adaptor+ distal tip" against malevolent attempts to disconnect the adaptor from the distal tip. Indeed, once the adaptor of the invention is mounted on the distal tip of a drug delivery device with the retaining means in their locked configuration, if a person tries to pull out the adaptor from the distal tip in the distal direction, this will only increase the compression exerted by the compressing means onto the retaining means. Once mounted, with the retaining means in their locked configuration, the adaptor may not be disconnected from the distal tip without breaking and damaging the whole assembly.

For example, the presence of the compressing means of the adaptor of the invention allows also preventing the adaptor from rotating with respect to the distal tip, once the retaining means are in their locked configuration. Additionally, some locking means could be formed on a proximal outer surface of the distal tip, preferably aligned on the longitudinal axis of the drug delivery device. These locking means may have the form of ribs that would lock the adaptor firmly in rotation thanks to a mechanical abutment of the radially outwardly deflectable tabs. Indeed, these ribs would fit closely within the space existing between two adjacent radially outwardly deflectable tabs in order to prevent any rotative movement of the adaptor.

Alternatively, the adaptor of the invention may be used with a conventional conical distal tip made of glass material without requiring that the shape or the outer surface of said distal tip be modified, for example by providing it with an annular groove or an annular ridge.

In one embodiment, the retaining means comprise one or more radially outwardly deflectable tabs distributed along the circumference of said inner ring, said tabs being in contact with an outer surface of said distal tip, when the adaptor is mounted on the distal tip, and the compressing means comprise an outer ring capable of receiving at least partially said radially outwardly deflectable tabs. The radial inward force exerted by the retaining means is therefore well distributed along the circumference of the distal tip, and the fixation is ensured.

In another embodiment, said radially outwardly deflectable tabs comprising proximal thin walls and distal thick walls, said outer ring comprises an inner radial rim, said inner radial rim facing said proximal thin walls and exerting no centripetal pressure thereon when said outer ring is in its proximal position, said inner radial rim being in contact with said distal thick walls and exerting a centripetal pressure thereon, when said outer ring is in its distal position.

In particular, the thick distal walls of the radially outwardly deflectable tabs provide the inner ring with good mechanical properties at the location where the connector is intended to be connected to the adaptor, for example by screwing. The connecting step, for example the screwing step, of the connector is therefore facilitated and may be safely performed.

The inner radial rim of the outer ring provides additional rigidity and mechanical property to the part of the outer ring intended to be in contact with the retaining means in order to exert an optimal centripetal pressure on said retaining means.

The inner ring may be made of a material selected from acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE) and their combinations. The outer ring may also be made of a material selected from acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE) and their combinations.

In one embodiment, the outer ring is preferably made from a material more rigid than the material forming the inner ring. For example, the outer ring, and in particular the inner radial rim, may be made of polyamide and the radially outwardly deflectable tabs may be made of polyethylene. In other embodiments, the outer ring, and in particular the inner radial rim, may be made of polybutylene terephthalate and the radially outwardly deflectable tabs may be made of thermoplastic elastomer.

In another embodiment, said connecting means are located on the inner ring. For example, the connecting means comprises a thread provided on an inner wall of said inner ring.

The adaptor comprises releasable maintaining means for temporarily maintaining said compressing means in its proximal position with respect to said retaining means. The adaptor may therefore be handled in a pre-assembled position, in which the compressing means are in their proximal position with respect to said retaining means. For example, the releasable maintaining means allow the outer ring to be maintained temporarily in its proximal position with respect to the radially outwardly deflectable tabs. The handling of the adaptor of the invention is therefore simplified for the user, who may simply mount the adaptor in the pre-assembled position onto the distal tip of the drug delivery device with the guaranty that the inner ring and the compressing means are correctly positioned one with respect to the other. The pre-assembled position of the adaptor also simplifies, for the user, the step of moving the compressing means from its proximal position to its distal position. Therefore, the user needs to perform only one single and simple operation in order to move the retaining means in their locked configuration.

In yet another embodiment, the adaptor further comprises snap-fitting means for securing said compressing means in its distal position with respect to the retaining means. The retaining means are therefore safely fixed in their locked configuration: as a consequence, once the adaptor is mounted on the distal tip, it may not get detached therefrom.

Another aspect of the present invention is a drug delivery device comprising a distal tip defining an axial passage-way for the transfer of a product contained in said drug delivery device, characterized in that it further comprises at least one adaptor as previously described.

The distal tip is made of glass.

The distal tip is conical and distally tapered: the radial inward force exerted by the radially outwardly deflectable tabs in their free configuration is therefore increased.

In embodiments, the distal tip being provided with an annular ridge defining a proximal outer surface and a distal outer surface of said distal tip, said retaining means exert said radial inward force on said proximal outer surface when said adaptor is mounted on said distal tip.

The annular ridge forms an additional obstacle to the potential detachment of the adaptor from the distal tip, once the adaptor is mounted on said distal tip.

In another embodiment, a proximal region of the outer surface of the distal tip is provided with locking means intended to cooperate with the retaining means so as to prevent the rotation of said adaptor with respect to said distal tip when the adaptor is mounted on said distal tip. These locking means may have the form of ribs that would lock the adaptor firmly in rotation thanks to a mechanical abutment of the radially outwardly deflectable tabs.

Another aspect of the present invention is a method for mounting an adaptor as previously described on the distal tip of a drug delivery device as previously described, said method comprising at least the following steps:
providing the adaptor with the compressing means in their proximal position with respect to the retaining means, engaging said adaptor onto the distal tip via the inner ring until the adaptor is correctly positioned on the distal tip, moving the compressing means with respect to the retaining means from their proximal position to their distal position.

BRIEF DESCRIPTION OF THE DRAWINGS

The invention and the advantages arising therefrom will clearly emerge from the detailed description that is given below with reference to the appended drawings in which:

FIG. 1 is an exploded perspective view from the top of an embodiment of the adaptor of the invention, FIG. 2 is an exploded perspective view from the bottom of the adaptor of FIG. 1, FIG. 3 is an exploded cross section view of the adaptor of FIG. 1, FIG. 4 is a cross section view of a drug delivery device and adaptor of the invention, before the adaptor of FIGS. 1-3 is mounted onto the distal tip of the drug delivery device, FIG. 5 is a cross sectional view of the drug delivery device and adaptor of FIG. 4, when the outer ring is in its proximal position with respect to the retaining means, at the beginning of the engagement of the inner ring on the distal tip, FIG. 6 is a cross section view of the drug delivery device and adaptor of FIG. 4, when the adaptor is correctly positioned on the distal tip, with the retaining means still in their free configuration, FIG. 7 is a cross section view of the drug delivery device and adaptor of FIG. 4, with the adaptor mounted on the distal tip, with the outer ring in its distal position and the retaining means in their locked configuration.

With reference to FIGS. 1-3, is shown an adaptor 10 of the invention, comprising an inner ring 20 and an outer ring 30, intended to be mounted on a drug delivery device 1 provided at its distal end with a distal tip 2 (see FIG. 4).

DETAILED DESCRIPTION OF THE INVENTION

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the drug delivery device the adaptor of the invention is intended to be mounted on, and the "proximal direction" is to be understood as meaning the opposite direction to said direction of injection.

With reference to FIGS. 1-3, the inner ring 20 comprises a circular wall 21 provided at its distal end with an outer radial rim 22 formed of a plurality of circumferential distributed outer projections 22a in the example shown. The circular wall 21 is also provided on its outer face with an annular outer ridge 23. The outer radial rim 22 and the annular outer ridge 23 define in between them an annular groove 24. The circular wall 21 is further provided with a proximal annular groove 29, distally spaced from the annular outer ridge 23. The circular wall 21 is provided at its proximal end with a plurality of radially outwardly deflectable tabs 25, extending in the proximal direction, and regularly distributed along the circumference of the circular wall 21.

On the example shown, the inner ring 20 comprises eight such radially outwardly deflectable tabs 25. In examples not shown, the inner ring 20 may comprise less or more of these radially outwardly deflectable tabs 25, such as four, five or nine or ten. The plurality of radially outwardly deflectable tabs 25 define a central hole 26 shaped and dimensioned in order to allow the engagement of the inner ring 20 on the distal tip 2 (see FIG. 5) of the drug delivery device 1.

On FIG. 1, the radially outwardly deflectable tabs 25 are submitted to no strain and are therefore in a rest position.

Each radially outwardly deflectable tab 25 is provided with an outer face which is proximally tapered. In addition, each radially outwardly deflectable tab 25 is provided in the distal area of its inner wall with an inner radial projection 28. As a consequence, the wall of each radially outwardly deflectable tab 25 is thicker in its distal region than in its proximal region. In other words, each radially outwardly deflectable tab 25 is provided with a thick distal wall 25a and a thin proximal wall 25b.

As shown on FIG. 2, a thread 27 is provided on the inner face of the circular wall 21. As will appear from the following description, this thread 27 forms a connecting means for connecting the adaptor 10 to a connector (not shown) at the time of use of the drug delivery device 1.

In an embodiment not shown, the connecting means can be a groove provided on the inner face of the circular wall of the inner ring, in which a connector may be clipped.

The outer ring 30 comprises a circular wall 31 provided at its proximal end with an inner radial rim 32. The circular wall 31 of the outer ring 30 is dimensioned and shaped so as to be capable of receiving the circular wall 21 of the inner ring 20, but not the outer radial rim 22 of said inner ring 20. As a consequence, as will appear later from the description of FIG. 7, the outer radial rim 22 is in proximal abutment on the distal end of the circular wall 31 of the outer ring 30 once the adaptor 10 is mounted on the distal tip 2.

In addition, the inner radial rim 32 of the outer ring 30 defines a central hole 33: the diameter of this central hole 33 is greater than the outer diameter of the distal tip 2 (see FIG. 4) and is also slightly greater than the outer diameter defined by the outer faces of the thin proximal walls 25b of the plurality of the radially outwardly deflectable tabs 25. In addition, the diameter of the central hole 33 is smaller than the outer diameter defined by the outer faces of the thick distal walls 25a of the plurality of the radially outwardly deflectable tabs 25.

The outer ring 30 is further provided at its distal end with an inner annular ridge 34, formed of three ridge segments 34a on the example shown on FIG. 2.

The inner ring 20 and the outer ring 30 may be made of a material selected from acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE) and their combinations.

Anyway, as will appear from the description below, as the outer ring 30, and in particular its inner radial rim 32, is intended to compress inwardly radially the radially outwardly deflectable tabs 25 when the adaptor 10 is mounted on the distal tip 2 (see FIG. 7), so that all axial movement of the adaptor 10 is limited or prevented, the inner radial rim 32 is preferably made from a material more rigid than the material forming the radially outwardly deflectable tabs 25.

For example, in embodiments, the outer ring 30, and in particular the inner radial rim 32, is made of polyamide and the radially outwardly deflectable tabs 25 are made of polyethylene.

In other embodiments, the outer ring 30, and in particular the inner radial rim 32, may be made of polybutylene terephthalate and the radially outwardly deflectable tabs 25 may be made of thermoplastic elastomer.

For example, the inner diameter of the inner radial rim 32 of the outer ring may be smaller, for example 0.4 mm smaller, than the outer diameter defined by the radially outwardly deflectable tabs 25.

As will appear in the description later, the adaptor 10 is intended to be engaged on the distal tip of a drug delivery device in a pre-assembled position (shown on FIG. 5). In this pre-assembled position of the adaptor 10, the circular wall 21 is received in the outer ring 30, the thin proximal walls 25*b* of the radially outwardly deflectable tabs 25 face the inner radial rim 32 of the outer ring 30, and the inner annular ridge 34 of the outer ring 30 is engaged in the proximal annular groove 29 of the inner ring 20.

The mounting of the adaptor 10 on the distal tip 2 of a drug delivery device 1 will now be described with reference to FIGS. 4-7.

With reference to FIG. 4 is shown the adaptor 10, in a position where the inner ring 20 and the outer ring 30 are not yet assembled, and a drug delivery device 1 provided with a distal tip 2.

The drug delivery device 1 and the adaptor 10 are aligned and have a common longitudinal axis A. The distal tip 2 is conical and distally tapered and it defines an axial passageway 3 for the transfer of a product (not shown) contained or intended to be contained in the drug delivery device 1. The axial passageway 3 is open at its distal end 3*a*. In embodiments not shown, the distal tip may have a cylindrical outer surface.

On FIG. 4 is also shown a cap 40 comprising a rubber plug 41 and a rigid sleeve 42 capable of receiving the rubber plug 41. As shown in the following description, the cap 40 is intended to close the open distal end 3*a* of the passageway 3 of the distal tip 2 of the drug delivery device 1, when the drug delivery device 1 is not in use but serves as a storage container of the product. As shown in the following description, the cap 40 is not part of the invention, and is intended to be removed at the time of use of the drug delivery device 1: indeed, when a user wishes to transfer the product from the drug delivery device 1 into another medical device (such as a infusion line, another syringe, etc . . . ), the cap 40 is replaced by a connector (not shown) allowing the transfer of the product from the drug delivery device 1 to said other medical device.

On the example shown on the Figures, the distal tip 2 is provided with an annular ridge 4 defining a distal outer surface 2*a* and a proximal outer surface 2*b* of the distal tip 2. In embodiments not shown, the outer surface of the distal tip 2 may be free of any annular ridge, or alternatively may be provided with an annular groove or with an inverted cone.

The distal tip 2 may be made of plastic or glass material. In embodiments, the distal tip 2 is made of glass material. In another embodiment, the distal tip 2, as well as the drug delivery device, is made of plastic material selected from crystal clear polymer (CCP), acrylonitrile butadiene styrene (ABS), polycarbonate (PC), polystyrene (PS), polypropylene (PP), polyethylene (PE), polyamide (PA) and their combinations.

FIGS. 4-7 show the mounting of the adaptor 10 on the distal tip 2 of the drug delivery device 1 so as to obtain on FIG. 7 the drug delivery device 1 in a storage position. As a consequence, the cap 40 is mounted on the drug delivery device 1 so as to close the distal end 3*a* of the distal tip 3, the thread 27 forming a connecting means for connecting the cap 40 to the inner ring 20, by cooperating with an outer thread 43 provided on the outer wall of the rigid sleeve 42.

Anyway, as said, the cap 40 is not part of the adaptor 10 of the invention and is intended to be replaced with a connector (not shown) provided with a thread capable of cooperating the thread 27 of the inner ring 10, in view of transferring product from the drug delivery device 1 to another medical device.

On FIG. 4, the inner ring 20 of the adaptor 10 is not engaged yet on the distal tip 2, and the radially outwardly deflectable tabs 25 are not submitted to any strain and are therefore in a rest position.

With reference to FIG. 5, the inner ring 20 is received within the outer ring 30, with the inner radial rim 32 of the outer ring 30 facing the thin proximal walls 25*b* of the radially outwardly deflectable tabs 25, and the inner annular ridge 34 of the outer ring 30 engaged in the proximal annular groove 29 of the inner ring 20. The inner annular ridge 34 and the proximal annular groove 29 form releasable maintaining means for maintaining the outer ring 30 and the inner ring 20 in a pre-assembled position of the adaptor 10. In this position of the outer ring 30, the inner radial rim 32 does not exert any pressure on the thin proximal walls 25*b* of the radially outwardly deflectable tabs 25, which are in their rest position. The outer ring 30 is in its proximal position with respect to the retaining means, in other words the radially outwardly deflectable tabs 25.

Then, the user approaches the adaptor 10 to the distal end of the distal tip 2 and starts to engage the adaptor 10, via its inner ring 20, on the distal tip 2, as shown on FIG. 5. As the distal tip 2 is distally tapered, when the user pushes the adaptor 10 in the proximal direction, the radially outwardly deflectable tabs 25 come in contact with the outer surface of the distal tip 2: as a consequence, they deflect radially outwardly until the user positions the adaptor 10 correctly, with the radially outwardly deflectable tabs 25 facing the proximal outer surface 2*b* on the example shown on FIG. 6. With reference to this Figure, in this position, the outer ring 30 is still in its proximal position with respect to the radially outwardly deflectable tabs 25. As a consequence, although the radially outwardly deflectable tabs 25 have deflected radially outwardly and do exert a radial inward force on the outer proximal surface 2*b* of the distal tip 2, they are still in their free configuration, and said radial inward force does not limit the axial movement of said adaptor 10 with respect to said distal tip 2 if the user moves said adaptor 10 in the distal direction for example. At this stage, the adaptor 10 may still be removed from the distal tip 2 easily.

In addition, in the position shown on FIG. 6, although the radially outwardly deflectable tabs 25 have deflected radially outwardly, because the central hole 33 of the outer ring 30 has a greater diameter than the outer diameter defined by the outer faces of the thin proximal walls 25*b* of the plurality of radially outwardly deflectable tabs 25, the inner radial rim 32 of the outer ring 30 does not apply any centripetal pressure on the radially outwardly deflectable tabs 25.

In a further step, the user then applies a proximal pressure on the inner ring 20, for example via the cap 40 on the example shown: this proximal pressure causes the inner annular ridge 34 of the outer ring 30 to escape from the proximal annular groove 29 of the inner ring 20, and the outer ring 30 is therefore moved from its proximal position to its distal position with respect to the radially outwardly deflectable tabs 25, as shown on FIG. 7: the inner radial rim 32 comes therefore in contact with the thick distal walls 25*a* of the radially outwardly deflectable tabs 25. Because of the variation of thickness between the proximal thin walls 25*b* and the distal thick walls 25*a*, the inner radial rim 32 now exerts a centripetal pressure on the distal thick walls 25*a* of the radially outwardly deflectable tabs 25. The outer ring 30, and in particular its inner radial rim 32, acts as a compressing means of the distal thick walls 25a of the radially outwardly deflectable tabs 25. As a consequence, the radial inward force now exerted by the radially outwardly deflectable tabs 25 on the distal tip 2 via its distal thick walls 25a has been increased from additional centripetal pressure originating from the inner radial rim 32. The radially outwardly deflectable tabs 25 are now in their locked position, and the radial inward force they now exert on the distal tip 2 limits any potential axial movement of the adaptor 10 with respect to the distal tip 2. In embodiments, the radial inward force from the radially outwardly deflectable tabs 25 now exerted on the distal tip 2 may also prevent any rotation of the inner ring 20 and of the adaptor 10 with respect to the distal tip 2.

Additionally, in an embodiment not shown, some locking means could be formed on the proximal outer surface of the distal tip, preferably aligned on the longitudinal axis of the drug delivery device. These locking means can have the form of ribs that would lock the adaptor firmly in rotation thanks to a mechanical abutment with the radially outwardly deflectable tabs 25. Indeed, these ribs would fit closely within the space existing between two adjacent radially outwardly deflectable tabs in order to prevent any rotational movement of the adaptor with respect to the distal tip. Preferably at least two locking means would be required but the number of the locking means and their distribution on the surface of the distal tip may depend on the number of free spaces existing between two adjacent radially outwardly deflectable tabs 25.

In addition, as shown on FIG. 7, the inner annular ridge 34 of the outer ring 30 is now engaged in the annular groove 24 of the inner ring 20, thereby preventing axial movement of the inner ring 20 with respect to the outer ring 30. The inner annular ridge 34 of the outer ring 30 and the annular groove 24 of the inner ring 20 form snap-fitting means for securing the outer ring 30 in its distal position with respect to the radially outwardly deflectable tabs 25. The retaining means, in other words the radially outwardly deflectable tabs 25 are therefore safely maintained in their locked configuration.

As a consequence, the adaptor 10 is now firmly attached to the distal tip 2, and it may not be disconnected from said distal tip, even if a user tries to pull it out in a direction or the other.

For using the drug delivery device 1, the user only needs to remove the cap 40 by unscrewing it from the inner ring 20. This step is easy to complete thanks to the secured fixation of the adaptor 10 to the distal tip 2. In particular, the user knows that the removal of the cap 40 can be done safely and may not cause the adaptor 10 to be separated from the distal tip 2. Once the cap 40 is removed, the user may then screw on thread 27 a corresponding outer thread provided on a connector (not shown) in order to proceed to the transfer of the product contained in the drug delivery device to another medical device via the connector.

Again, because of the secured fixation of the adaptor 10 on the distal tip 2, the connection of the connector to the adaptor 10, and therefore to the distal tip 2 is facilitated.

The adaptor of the invention allows the reliable connection of a connector on the distal tip of a drug delivery device, without having to modify the shape and/or the outer surface of said distal tip. The risks that the adaptor of the invention be displaced and eventually misplaced on the distal tip of the drug delivery device and that the connector be wrongly connected are greatly limited.

The invention claimed is:

1. An adaptor for mounting on a distal tip of a drug delivery device, said distal tip defining an axial passage-way for the transfer of a product contained in said drug delivery device, said adaptor having a longitudinal axis aligned on said axial passageway, the adaptor configured to be connected to a connector, said adaptor further comprising:
   an inner ring capable of being engaged on said distal tip, said inner ring comprising a retainer capable of exerting a radial inward force on said distal tip once said adaptor is engaged on said distal tip,
   wherein, when said inner ring is engaged on said distal tip, said retainer is capable of transitioning from a free configuration, in which the radial inward force said retainer exerts on said distal tip does not limit an axial movement of said adaptor with respect to said distal tip, to a locked configuration, in which the radial inward force said retainer exerts on said distal tip limits said axial movement,
   wherein the inner ring defines a proximal annular groove and a distal annular groove spaced apart from the proximal annular groove,
   the adaptor further comprising:
   a compression element configured to transition between:
      a first position in which said compression element is not coupled with said inner ring;
      a second position in which said compression element is coupled with said inner ring in a proximal position in which said compression element does not exert a centripetal pressure on said retainer and said retainer is in the free configuration; and
      a third position in which said compression element is coupled with said inner ring in a distal position in which said compression element exerts a centripetal pressure on said retainer and said retainer is in the locked configuration, wherein the compression element is configured to be movable axially with respect to the retainer while coupled to the inner ring between the second position and the third position, and
   a releasable restraining element configured to engage the proximal annular groove to temporarily maintain said compression element in the second position and, upon application of sufficient axial pressure, the releasable restraining element is configured to escape the proximal annular groove and transition into the distal annular groove to maintain the third position.

2. The adaptor according to claim 1, wherein the retainer comprises one or more radially outwardly deflectable tabs distributed along the circumference of said inner ring, said tabs being in contact with an outer surface of said distal tip when the adaptor is mounted on the distal tip, and the compression element comprises an outer ring capable of at least partially receiving said radially outwardly deflectable tabs.

3. The adaptor according to claim 2, wherein, said radially outwardly deflectable tabs comprise a proximal thin wall and distal thick wall, said outer ring comprises an inner radial rim, said inner radial rim facing said proximal thin wall and exerting no centripetal pressure thereon when said outer ring is in the second position, said inner radial rim being in contact with said distal thick wall and exerting a centripetal pressure thereon, when said outer ring is in the third position.

4. The adaptor according to claim 1, wherein the inner ring of the adaptor is configured to be connected to the connector.

5. The adaptor according to claim 4, wherein an inner wall of the inner ring comprises a thread configured to connect the adaptor to the connector.

6. The adaptor according to claim 1, further comprising a snap-fit connection for securing said compression element in the third position with respect to the retainer.

7. A drug delivery device comprising a distal tip defining an axial passage-way for the transfer of a product contained in said drug delivery device, and an adaptor mountable on the distal tip, the adaptor having a longitudinal axis aligned on said axial passageway, the adaptor configured to be connected to a connector, said adaptor further comprising:
 an inner ring capable of being engaged on said distal tip, said inner ring comprising a retainer capable of exerting a radial inward force on said distal tip once said adaptor is engaged on said distal tip,
 wherein, when said inner ring is engaged on said distal tip, said retainer is capable of transitioning from a free configuration, in which the radial inward force said retainer exerts on said distal tip does not limit an axial movement of said adaptor with respect to said distal tip to a locked configuration, in which the radial inward force said retainer exerts on said distal tip limits said axial movement,
 wherein the inner ring defines a proximal annular groove and a distal annular groove spaced apart from the proximal annular groove,
 the adaptor further comprising:
  a compression element configured to transition between:
  a first position in which said compression element is not coupled with said inner ring;
  a second position in which said compression element is coupled with said inner ring in a proximal position in which said compression element does not exert a centripetal pressure on said retainer and said retainer is in the free configuration; and
  a third position in which said compression element is coupled with said inner ring in a distal position in which said compression element exerts a centripetal pressure on said retainer and said retainer is in the locked configuration, wherein the compression element is configured to be movable axially with respect to the retainer while coupled to the inner ring between the second position and the third position, and
  a releasable restraining element configured to engage the proximal annular groove to temporarily maintain said compression element in the second position and, upon application of sufficient axial pressure, the releasable restraining element is configured to escape the proximal annular groove and transition into the distal annular groove to maintain the third position.

8. The drug delivery device according to claim 7, wherein the distal tip is made of glass.

9. The drug delivery device according to claim 7, wherein the distal tip is conical and distally tapered.

10. The drug delivery device according to claim 7, wherein the distal tip is provided with an annular ridge and defines a proximal outer surface and a distal outer surface of said distal tip, wherein said retainer exerts said radial inward force on said proximal outer surface when said adaptor is mounted on said distal tip.

11. The drug delivery device according to claim 10, wherein a proximal region of the outer surface of said distal tip is provided with a lock configured to cooperate with said retainer so as to prevent the rotation of said adaptor with respect to said distal tip when said adaptor is mounted on said distal tip.

12. A method for mounting an adaptor on a distal tip of a drug delivery device wherein said distal tip defines an axial passageway for the transfer of a product contained in said drug delivery device, and said adaptor is mountable on the distal tip, said adaptor having a longitudinal axis aligned on said axial passageway, said adaptor configured to be connected to a connector, said adaptor further comprising:
 an inner ring capable of being engaged on said distal tip, said inner ring comprising a retainer capable of exerting a radial inward force on said distal tip once said adaptor is engaged on said distal tip, wherein,
 when said inner ring is engaged on said distal tip, said retainer is capable of transitioning from a free configuration, in which the radial inward force said retainer exerts on said distal tip does not limit an axial movement of said adaptor with respect to said distal tip, to a locked configuration, in which the radial inward force said retainer exerts on said distal tip limits said axial movement,
 wherein the inner ring defines a proximal annular groove and a distal annular groove spaced apart from the proximal annular groove,
 the adaptor further comprising:
 a compression element configured to transition between:
 a first position in which said compression element is not coupled with said inner ring;
 a second position in which said compression element is coupled with said inner ring in a proximal position in which said compression element does not exert a centripetal pressure on said retainer and said retainer is in the free configuration; and
 a third position in which said compression element is coupled with said inner ring in a distal position in which said compression element exerts a centripetal pressure on said retainer and said retainer is in the locked configuration, wherein the compression element is configured to be movable axially with respect to the retainer while coupled to the inner ring between the second position and the third position, and
 a releasable restraining element configured to engage the proximal annular groove to temporarily maintain said compression element in the second position and, upon application of sufficient axial pressure, the releasable restraining element is configured to escape the proximal annular groove and transition into the distal annular groove to maintain the third position comprising the steps of:
 providing the compression element in the second position with respect to the retainer,
 engaging said adaptor onto the distal tip via the inner ring until the adaptor is correctly positioned on the distal tip, and
 moving the compression element with respect to the retainer from the second position to the third position.

13. The adaptor of claim 1, wherein the releasable restraining element comprises a projection provided on an interior portion of the compression element.

* * * * *